(12) United States Patent
Tung et al.

(10) Patent No.: US 7,544,324 B2
(45) Date of Patent: Jun. 9, 2009

(54) RAPID SAMPLE ANALYSIS STORAGE DEVICES AND METHODS OF USE

(75) Inventors: Hsiaoho Edward Tung, San Diego, CA (US); Yuzhang Wu, Hangzhou (CN); Jielin Dai, Hangzhou (CN); Ying Yang, Hangzhou (CN)

(73) Assignee: Oakville Hong Kong Company Limited, Central (HK)

( * ) Notice: Subject to any disclaimer, the term of this patent is extended or adjusted under 35 U.S.C. 154(b) by 792 days.

(21) Appl. No.: 10/990,324

(22) Filed: Nov. 15, 2004

(65) Prior Publication Data

US 2005/0180882 A1 Aug. 18, 2005

Related U.S. Application Data

(60) Provisional application No. 60/520,437, filed on Nov. 14, 2003.

(51) Int. Cl.
| | |
|---|---|
| G01N 21/00 | (2006.01) |
| G01N 9/30 | (2006.01) |
| G01N 31/22 | (2006.01) |
| G01N 33/48 | (2006.01) |

(52) U.S. Cl. .............................. 422/56; 422/64; 422/72; 422/102; 436/165

(58) Field of Classification Search .................. 422/56, 422/64, 72, 102; 436/165
See application file for complete search history.

(56) References Cited

U.S. PATENT DOCUMENTS

| | | | |
|---|---|---|---|
| 3,896,974 A | 7/1975 | McIntosh | |
| 4,114,605 A | 9/1978 | McGhee et al. | |
| 4,275,149 A | 6/1981 | Litman et al. | |
| 4,299,916 A | 11/1981 | Litman et al. | |
| 4,458,020 A | * 7/1984 | Bohn et al. ............... 435/287.2 | |
| 4,635,488 A | 1/1987 | Kremer | |
| 4,768,238 A | 9/1988 | Kleinberg et al. | |
| 4,771,486 A | 9/1988 | Gutierrez et al. | |
| 4,817,632 A | 4/1989 | Schramm | |
| 4,853,325 A | 8/1989 | Vodian et al. | |
| 4,886,175 A | 12/1989 | Schlaudecker | |

(Continued)

FOREIGN PATENT DOCUMENTS

EP 0 390 984 A1 10/1990

(Continued)

*Primary Examiner*—Jill Warden
*Assistant Examiner*—Lore Ramillano
(74) *Attorney, Agent, or Firm*—Fred C. Hernandez; Mintz, Levin, Cohn, Ferris, Glovsky and Popeo, P.C.

(57) ABSTRACT

The present invention provides test devices for detecting an analyte suspected of being present in a liquid sample. The devices contain a reservoir compartment, a test compartment, and a port for a sample collection well. The devices also have a rotatable sample collection well located in the port. The device has an upper chamber for insertion of a sample applicator, an expression plate for wringing out the sample applicator and applying sample to the device, a lower chamber, and an aliquot outlet and a reservoir outlet for the movement of sample through the device. The device also contains test elements for detecting the analyte of interest. By rotating the sample collection well, the operator is able to direct distribution of collected sample in the device. Methods of using the devices and kits containing the devices are also provided.

19 Claims, 8 Drawing Sheets

U.S. PATENT DOCUMENTS

| | | | |
|---|---|---|---|
| 4,923,798 A | 5/1990 | LeMoine et al. | |
| 4,955,745 A | 9/1990 | Vauquelin | |
| 5,050,616 A | 9/1991 | Wolff et al. | |
| 5,076,474 A | 12/1991 | Hansen | |
| 5,211,182 A | 5/1993 | Deutsch et al. | |
| 5,246,145 A | 9/1993 | Leoncavallo et al. | |
| 5,260,031 A | 11/1993 | Seymour | |
| 5,261,572 A | 11/1993 | Strater | |
| 5,328,058 A | 7/1994 | Leoncavallo et al. | |
| 5,334,502 A | 8/1994 | Sangha | |
| 5,339,829 A | 8/1994 | Thieme et al. | |
| 5,376,337 A | 12/1994 | Seymour | |
| 5,380,492 A | 1/1995 | Seymour | |
| 5,393,496 A | 2/1995 | Seymour | |
| 5,479,937 A | 1/1996 | Thieme et al. | |
| 5,494,646 A | 2/1996 | Seymour | |
| 5,573,009 A | 11/1996 | Thieme et al. | |
| 5,609,160 A | 3/1997 | Bahl et al. | |
| 5,714,341 A | 2/1998 | Thieme et al. | |
| 5,736,322 A | 4/1998 | Goldstein | |
| 5,786,227 A | 7/1998 | Charlton | |
| 5,786,228 A | 7/1998 | Charlton | |
| 5,830,410 A | 11/1998 | Thieme et al. | |
| 5,910,122 A | 6/1999 | D'Angelo | |
| 5,935,864 A | 8/1999 | Schramm | |
| 5,965,453 A | 10/1999 | Skiffington | |
| 5,968,746 A | 10/1999 | Schneider | |
| 5,981,293 A | 11/1999 | Charlton | |
| 5,981,300 A | 11/1999 | Moll et al. | |
| 6,022,326 A | 2/2000 | Tatum et al. | |
| 6,102,872 A | 8/2000 | Doneen et al. | |
| 6,150,178 A | 11/2000 | Cesarczyk | |
| 6,223,947 B1 | 5/2001 | Bernard | |
| 6,241,689 B1 | 6/2001 | Chard et al. | |
| 6,248,598 B1 | 6/2001 | Bogema | |
| 6,277,587 B1 | 8/2001 | Lamster | |
| 6,277,646 B1* | 8/2001 | Guirguis et al. | 436/165 |
| 6,291,178 B1 | 9/2001 | Schneider | |
| 6,303,081 B1 | 10/2001 | Mink et al. | |
| 6,372,513 B1 | 4/2002 | Nguyen et al. | |
| 6,423,550 B1 | 7/2002 | Jenkins et al. | |
| 6,440,087 B1 | 8/2002 | Sangha | |
| 6,443,892 B1 | 9/2002 | Kidwell | |
| 6,464,939 B1 | 10/2002 | Bachand | |
| 6,468,474 B2 | 10/2002 | Bachand | |
| 6,489,172 B1 | 12/2002 | Bachand | |
| 7,481,977 B2* | 1/2009 | Percival et al. | 422/64 |
| 2001/0023324 A1 | 9/2001 | Pronovost et al. | |
| 2002/0004019 A1 | 1/2002 | Bachand et al. | |
| 2002/0015663 A1 | 2/2002 | Goldstein et al. | |
| 2002/0020713 A1 | 2/2002 | Kis et al. | |
| 2002/0085958 A1* | 7/2002 | Nemcek et al. | 422/102 |
| 2002/0146346 A1 | 10/2002 | Konecke | |
| 2002/0150884 A1 | 10/2002 | Zmuda et al. | |
| 2002/0155029 A1 | 10/2002 | Mink et al. | |
| 2002/0192839 A1 | 12/2002 | Mink et al. | |
| 2003/0064526 A1* | 4/2003 | Niedbala et al. | 436/165 |
| 2003/0129673 A1 | 7/2003 | Schwarz et al. | |
| 2003/0138971 A1 | 7/2003 | D'Aurora | |
| 2003/0175992 A1 | 9/2003 | Toranto et al. | |
| 2003/0175993 A1 | 9/2003 | Toranto et al. | |
| 2003/0190259 A1 | 10/2003 | Alley | |
| 2006/0292035 A1* | 12/2006 | Gould et al. | 422/58 |

FOREIGN PATENT DOCUMENTS

| | | |
|---|---|---|
| EP | 0 390 984 B1 | 10/1990 |
| EP | 0 392 096 A1 | 10/1990 |
| EP | 0392 096 B1 | 10/1990 |
| EP | 0 455 916 A2 | 11/1991 |
| EP | 0 455 916 A3 | 11/1991 |
| EP | 0 500 172 A1 | 8/1992 |
| EP | 0 542 107 A1 | 5/1993 |
| EP | 0561 322 A1 | 9/1993 |
| EP | 0 455 916 B1 | 2/1996 |
| EP | 0 561 322 B1 | 10/1996 |
| EP | 0 734 684 A1 | 10/1996 |
| EP | 0 734 685 A1 | 10/1996 |
| EP | 0 734 686 A1 | 10/1996 |
| EP | 0 753 148 B1 | 12/1998 |
| EP | 1 216 931 A1 | 6/2002 |
| EP | 1 275 962 A1 | 1/2003 |
| WO | WO 92/16842 | 10/1992 |
| WO | WO 93/11434 | 6/1993 |
| WO | WO 94/07419 | 4/1994 |
| WO | WO 94/18892 | 9/1994 |
| WO | WO 95/02822 | 1/1995 |
| WO | WO 95/07223 | 3/1995 |
| WO | WO 95/27205 | 10/1995 |
| WO | WO 97/20502 | 6/1997 |
| WO | WO 98/44158 | 10/1998 |
| WO | WO 99/06827 | 2/1999 |
| WO | WO 99/22639 | 5/1999 |
| WO | WO 99/22645 | 5/1999 |
| WO | WO 99/27139 | 6/1999 |
| WO | WO 99/50656 | 10/1999 |
| WO | WO 00/15020 | 3/2000 |
| WO | WO 00/20862 | 4/2000 |
| WO | WO 00/25666 | 5/2000 |
| WO | WO 00/64334 | 11/2000 |
| WO | WO 01/08993 A1 | 2/2001 |
| WO | WO 01/49820 A1 | 7/2001 |
| WO | WO 01/81915 A1 | 11/2001 |
| WO | WO 02/07645 A3 | 1/2002 |
| WO | WO 02/04942 A1 | 2/2002 |
| WO | WO 02/16946 A2 | 2/2002 |
| WO | WO 02/016946 A3 | 2/2002 |
| WO | WO 02/059600 A2 | 8/2002 |
| WO | WO 02/059600 A3 | 8/2002 |
| WO | WO 02/082040 A2 | 10/2002 |
| WO | WO 02/082040 A3 | 10/2002 |
| WO | WO 02/096480 A2 | 12/2003 |

* cited by examiner

RAPID SAMPLE ANALYSIS STORAGE DEVICES AND METHODS OF USE

This application claims priority to U.S. provisional patent application Ser. No. 60/520,437, filed Nov. 14, 2003, which is hereby incorporated by reference in its entirety, including all Tables, Figures and Claims.

FIELD OF THE INVENTION

The present invention is directed to devices for the collection and rapid analysis of fluids for analytes of interest.

BACKGROUND OF THE INVENTION

The following Background of the Invention is intended to aid the reader in understanding the invention and is not admitted to be prior art.

Illicit drug use is an established and growing problem in our society. In 2003, the US Department of Health and Human Services found that an estimated 19.5 million Americans or 8.2 percent of the population aged 12 or older, were current illicit drug users. Current illicit drug use means use of an illicit drug during the month prior to the US Department of Health and Human Services survey interview. Marijuana was found to be the most commonly used illicit drug, with a rate of 6.2 percent (14.6 million). An estimated 2.3 million persons (1.0 percent) were current cocaine users, 604,000 of whom used crack. Hallucinogens were used by 1.0 million persons, and there were an estimated 119,000 current heroin users.

To combat and monitor this problem, drug testing has become standard procedure in a variety of settings, such as employment, school, sports, law enforcement, and the like. To facilitate this effort, a drug-testing industry has emerged. This industry provides a variety of drug testing products. A typical product is a urine collection cup incorporating analysis tests. These devices can be complicated and difficult or messy to use, or they may pose special problems of sample adulteration by the subject trying to hide their recent drug abuse. In addition, urine samples cannot be collected in certain situations, such as on the road side or in public.

There is therefore a need for better methods and apparatuses for performing sample collection and testing.

SUMMARY OF THE INVENTION

The present invention provides test devices for detecting an analyte suspected of being present in a liquid sample. The devices contain a reservoir compartment, a test compartment, and a port for a sample collection well. The devices also have a rotatable sample collection well located in the port, a chamber for insertion of a sample applicator, an expression plate for wringing out the sample applicator and applying sample to the device, and an aliquot outlet and a reservoir outlet in the sample collection well for directing movement of sample through the device by rotating the sample collection well. The device also contains test elements for detecting the analyte of interest. By rotating the sample collection well, the operator is able to direct distribution of collected sample in the device by opening and/or closing outlets of the device. Methods of using the devices and kits containing the devices are also provided.

One aspect of the present invention is a test device for detecting an analyte suspected of being present in a liquid sample. The device has a casing having a reservoir compartment, a test compartment, and a port for a sample collection well. The device also has a rotatable sample collection well, situated in the port. In various embodiments the sample collection well can contain one or more of an upper chamber, an expression plate, a lower chamber, an aliquot outlet, and a reservoir outlet. At least one test element is contained in the test compartment. In various embodiments, one or more of these components contained within a casing. The sample collection well has a first position where fluid communication is provided through the reservoir outlet between the sample collection well and the reservoir compartment, and a second position where fluid communication is provided through the aliquot outlet between the sample collection well and the test element, and the reservoir outlet is closed. In one embodiment when the sample collection well is in the first position the aliquot outlet is closed, and when the sample collection well is in the second position, the reservoir outlet is closed. The sample collection well is turned or rotated between the two positions.

The term "reservoir compartment" refers to a sealable area of the apparatus in which fluid sample is stored and preserved from drying out or from contamination. The fluid sample can be stored in the reservoir compartment for confirmatory testing at a later time. The term "fluid communication" refers to the ability for liquid to flow and be transmitted between two areas which are in fluid communication. Thus, the collection well and the reservoir compartment are in fluid communication when fluid is able to flow from the collection well directly through the reservoir outlet and into the reservoir compartment. "Port" refers to the portion of the device or casing where the sample collection well interfaces with the casing, and can be placed into fluid communication with the test compartment and reservoir compartment by rotation of the sample collection well. The sample collection well can be inserted into the port as a separate part, or the sample collection well and casing can be manufactured as a single part. The sample collection well itself can be made of one part, or assembled from sub-parts.

The "aliquot outlet" is an aperture in the sample collection well that provides fluid communication between the sample collection well and the test compartment when the aliquot outlet is open. The "reservoir outlet" is an aperture in the sample collection well that provides fluid communication between the sample collection well and the reservoir compartment when the reservoir outlet is open. The aliquot outlet and reservoir outlets are both located in the sample collection well. In one embodiment both the aliquot and reservoir outlets are located in the lower compartment. The term "rotatable" refers to the ability of the sample collection well to be torsionally turned within the port. Rotation of the sample collection well results in the aliquot outlet or reservoir outlet being opened or closed.

In one embodiment the reservoir is in fluid communication with the lower chamber of the collection well through the reservoir outlet when the sample collection well is in the first position, and the test element is in fluid communication with the lower chamber of the collection well through the aliquot outlet when the sample collection well is in the second position. The lower compartment can be an area between the bottom of the rotatable sample collection well and the expression plate, and the aliquot outlet and the reservoir outlet can be situated on the bottom of the collection well. The sample collection well can also contain an aliquot seal, for sealing of the aliquot reservoir when the rotatable sample collection well is located in the second position. But sealing of the aliquot outlet and reservoir outlet can also be accomplished by the rotation of the sample collection well, which can close off the reservoir outlet and open the aliquot outlet.

In certain embodiments, the lower compartment is an area between the expression plate and the bottom of the rotatable sample collection well. In further embodiments, the aliquot outlet and the reservoir outlet are situated on the bottom of the collection well. Additionally, in some embodiments when the rotatable sample collection well is located in the second position, the collection well has an aliquot seal for sealing of the aliquot reservoir. In further embodiments, the port has a guide slot, and the rotatable sample collection well has a guide pin extending from its outer surface and movably located within the guide slot, for directing rotation of the sample collection well from the first position to the second position. The guide slot can be substantially parallel to the longitudinal axis of the test element. The "guide slot" is a slot or opening in the device, casing, or part attached to the casing which allows insertion of a guide pin or other protrusion from the sample collection well. When the guide pin is inserted into the guide slot, the sample collection well can be rotated in the port to effect opening or closing of the reservoir and/or aliquot outlets.

An "expression plate" refers to a surface where a sample applicator filled with fluid sample can be squeezed or crushed against to express sample from the applicator. The expression plate can have openings or holes to allow the passage of fluid sample from the applicator to the samplecollection well. The expression plate 340 can be located within the sample collection well 130, but can also be placed in another location where expressed sample will flow to the collection well 130. In one embodiment the expression plate 340 is located in the sample collection well 130 and divides the upper 518 and lower chambers 520, and has one or more holes or openings through which fluid sample can flow from the upper chamber 518 to the lower chamber 520. When the sample collector is pressed against the expression plate 340, sample flows through the opening in the expression plate 340, into the lower chamber 520.

In additional embodiments, the device or casing can have a window for observation of the test element and for determining the results of an assay. The device or casing can also have a sealable reservoir orifice for extracting liquid sample from the reservoir. Thus, sample may be conveniently removed from the reservoir, through the reservoir orifice, without need to disassemble the device. The reservoir orifice can be conveniently located on the casing, and is thus separately accessible without need to rotate the collection cup or insert any implements through the collection cup to access the preserved sample in the reservoir.

The "test element" can be any element that performs a test. In one embodiment, the test element is a test strip. The test strip may contain a member of a specific binding pair on the test strip for conducting an immunoassay. The test strip may be a chemical test strip that provides a detectable color change or other detectable signal when the assay is complete. A variety of samples can be used with the present invention including, but not limited to, a bodily fluid or a sample derived from a biological tissue or a bodily fluid. For example, the sample may be saliva, blood, serum, plasma, urine, feces, spinal fluid, vaginal swabs, mucus, and tissue.

A variety of analytes can be tested for with the present invention. The analyte may be an infectious agent or indicative of an infected state. The analyte may be a drug (for example a drug of abuse), a hormone, a protein, a nucleic acid molecule, an etiological agent and a specific binding member. The term "drug of abuse" (DOA) refers to a drug that is taken for non-medicinal reasons (usually for mind-altering effects). The abuse of such drugs can lead to physical and mental damage and (with some substances) dependence, addiction and/or death. Examples of DOAs include cocaine; amphetamines (e.g., black beauties, white bennies, dextroamphetamines, dexies, beans); methamphetamines (crank, meth, crystal, speed); barbiturates (Valium®, Roche Pharmaceuticals, Nutley, N.J.); sedatives (i.e. sleep-aids); lysergic acid diethylamide (LSD); depressants (downers, goofballs, barbs, blue devils, yellow jackets, ludes); tricyclic antidepressants (TCA, e.g., imipramine, amitriptyline and doxepin); phencyclidine (PCP); tetrahydrocannabinol (THC, pot, dope, hash, weed, etc.); and opiates (e.g., morphine, opium, codeine, heroin, oxycodone). Legal drugs that are taken for medical reasons, but on which overdose can easily occur may also be tested for using these test strips, for example, tricyclic antidepressants (imipramine and the like) and over the counter products containing acetaminophen.

In another aspect the present invention provides methods of detecting an analyte suspected of being present in a liquid sample. The methods involve applying a liquid sample suspected of containing the analyte to a sample applicator; applying the liquid sample to a test device disclosed herein by wringing or squeezing the sample applicator into the sample collection well, and detecting whether the analyte is present in the liquid sample.

In one embodiment the sample is applied to the sample applicator by placing the sample applicator into the mouth of the test subject, which thus becomes filled with saliva. The liquid sample is applied to the test device by pressing or squeezing the sample applicator against the expression plate of the device, and wringing the sample applicator out so that liquid sample flows into the sample collection well. In one embodiment the sample flows into the bottom chamber of the sample collection well. After the reservoir is filled with saliva, the sample collection well is then rotated from the first position to the second position to begin the assay.

In another aspect the present invention provides a test kit for detecting an analyte suspected of being present in a liquid sample. The test kit includes a device as described herein, and a sample applicator. The sample applicator can contain an absorbent portion, which may be made of a sponge or a foam. The sample applicator can be prepared by soaking in a solution designed to stimulate salivation in a test subject, thereby facilitating collection of saliva when placed into the mouth of a test subject. The kit can also include instructions for use of the device and sample applicator in the collection and determination of the presence of an analyte in saliva or oral fluid.

The summary of the invention described above is not limiting and other features and advantages of the invention will be apparent from the following detailed description, as well as from the claims.

DETAILED DESCRIPTION

In the following detailed description, reference is made to the accompanying drawings that form a part hereof, and in which is shown by way of illustration non-limiting specific embodiments in which the invention may be practiced. Other embodiments may be utilized and structural changes made without departing from the scope of the present invention.

The present device has several advantages over the prior art. The devices and methods of the present invention enable the easy detection of analytes in fluid samples. The devices also allow a quantity of sample to be easily stored for confirmatory testing at a later time, using a different principle of testing if desired. The confirmation sample is therefore safely stored from contamination. The device also allows the user to control the time of beginning the assay, because the present invention allows the user to apply sample to the sample collection well and fill the reservoir compartment, but the assay will not begin until the user rotates the sample collection well and thereby opens the aliquot outlet. FIGS. 1-8 show only certain embodiments of the present invention for purposes of illustrating the invention, and are not limiting. With reference to the present disclosure the person of ordinary skill will realize other embodiments.

Figure 1:
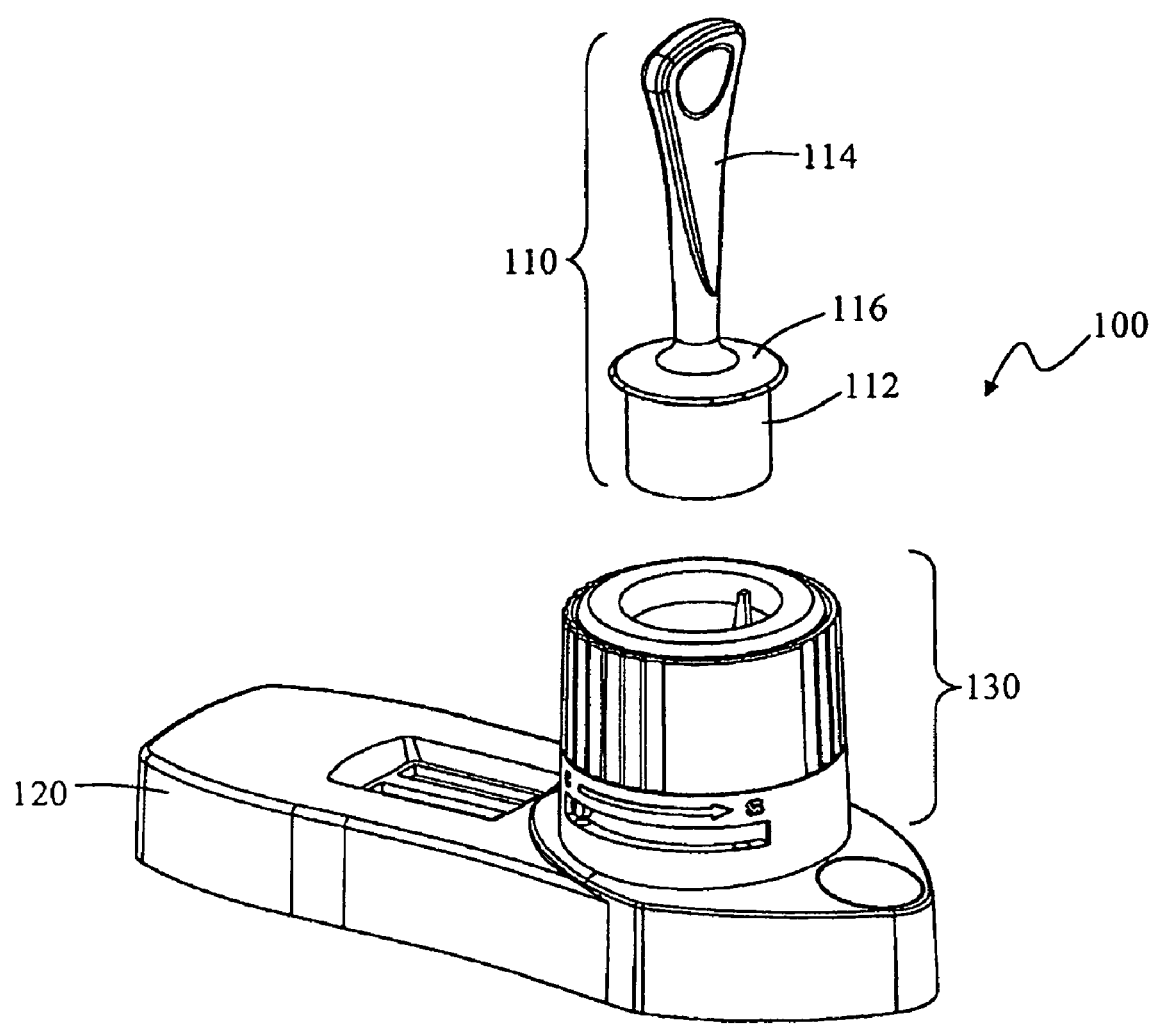
FIG. 1 provides a perspective view of one embodiment of the present invention 100.
Figure 3:
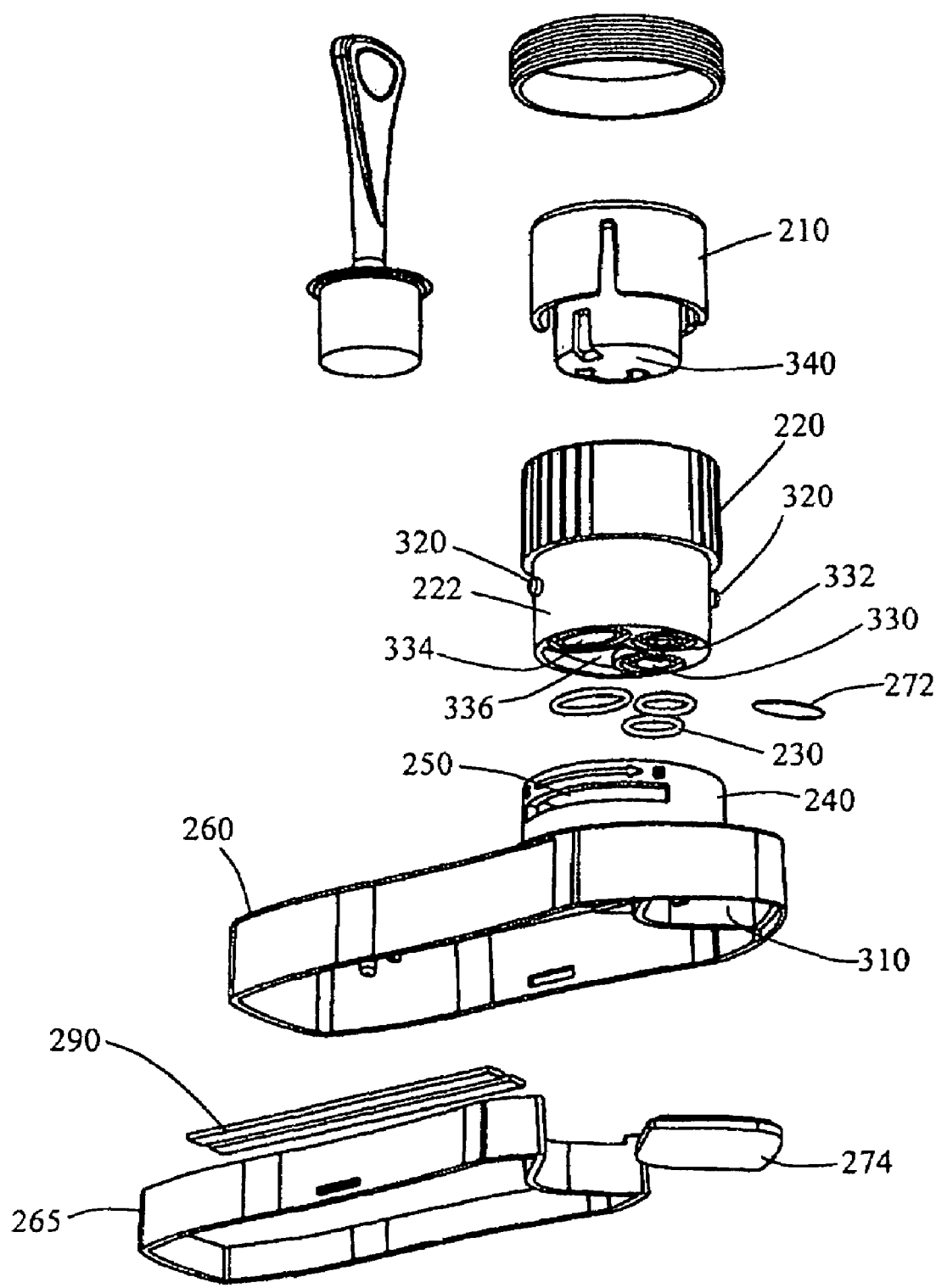
FIG. 3 provides another exploded view of the device of FIG. 1.
Figure 4:
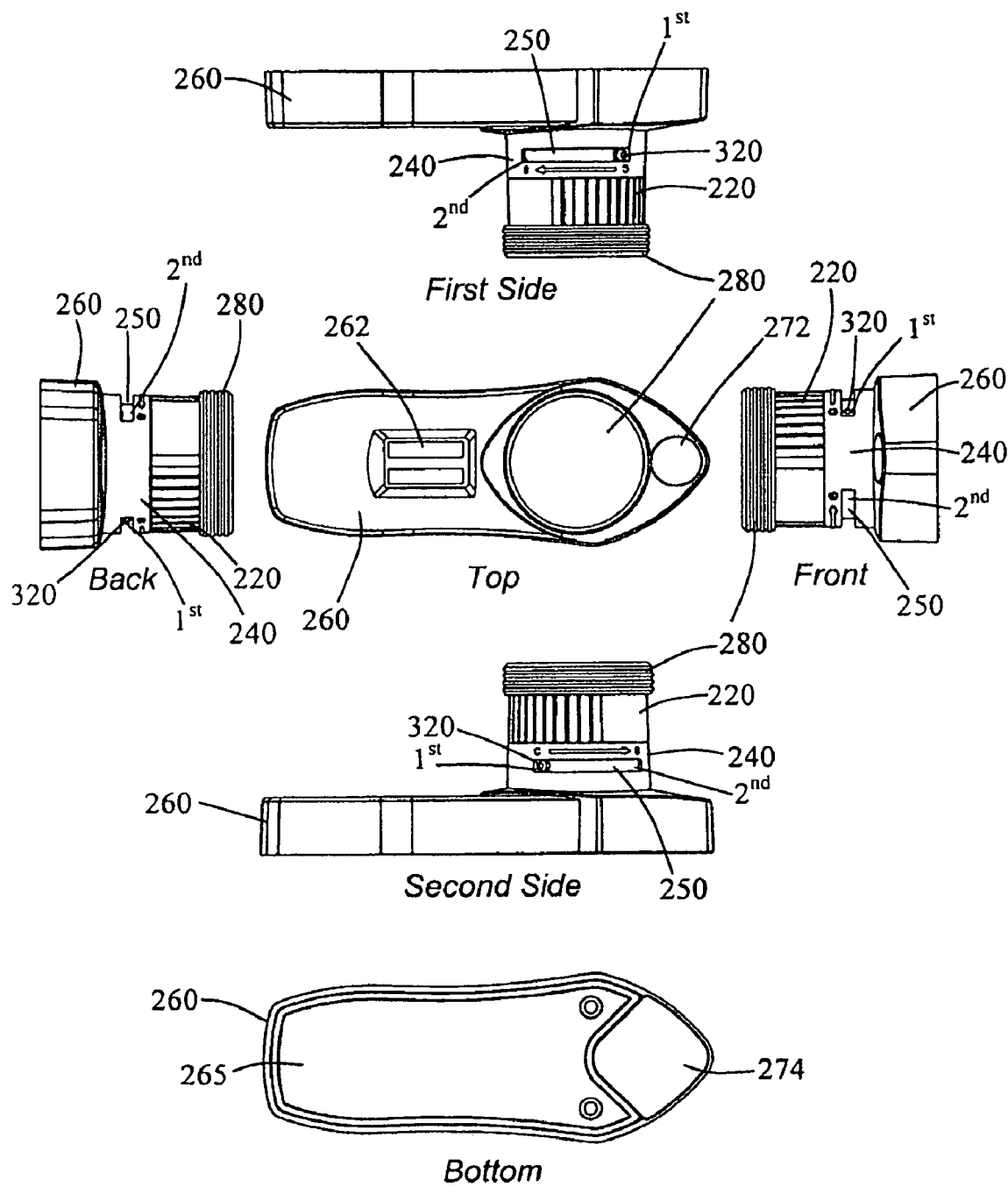
FIG. 4 show all six sides of the device of FIG. 1.
Figure 5:
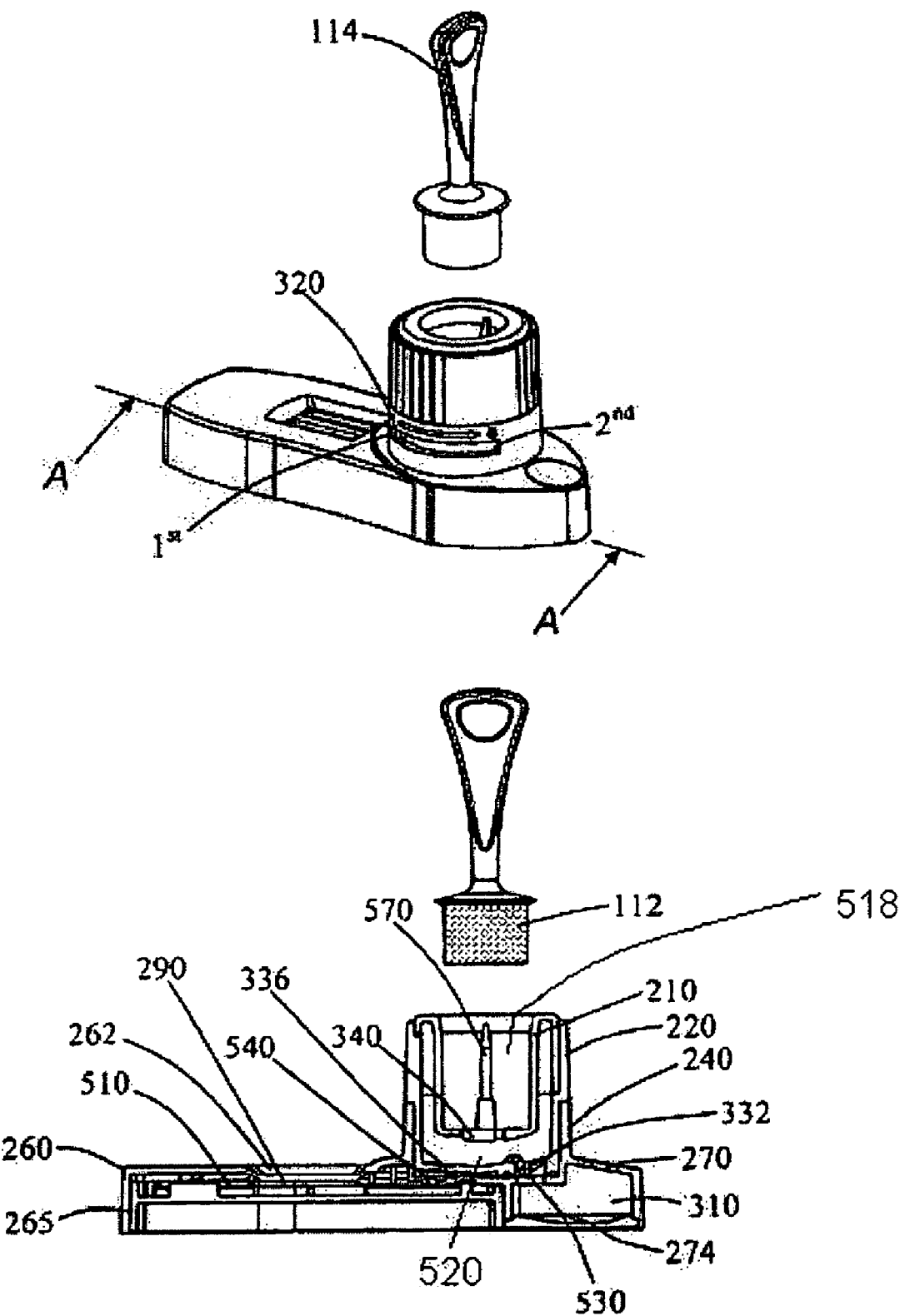
FIG. 5 provides an exterior view and a cut-away view of the device of FIG. 1, illustrating the state of the device prior to use.

With reference to FIG. 1, an embodiment of the invention is shown having a casing 120 and a sample collection well 130. A sample applicator 110 can also be supplied, having a rigid handle 114, a rim 116 and an absorbent member 112. In FIG. 5 it is shown that the casing can have two regions, a test compartment 510 and a reservoir compartment 310. With reference to FIG. 3, these two regions of the casing are defined by the forms of the injection-molded top portion 260 and bottom portion 265 of the casing, and the reservoir bottom 274. The different parts of the invention can conveniently be manufactured to snap together snugly. With reference to FIG. 3, test elements 290 are located within the test compartment. The reservoir 310 holds an aliquot of sample that can be used for confirmation testing.

Figure 2:
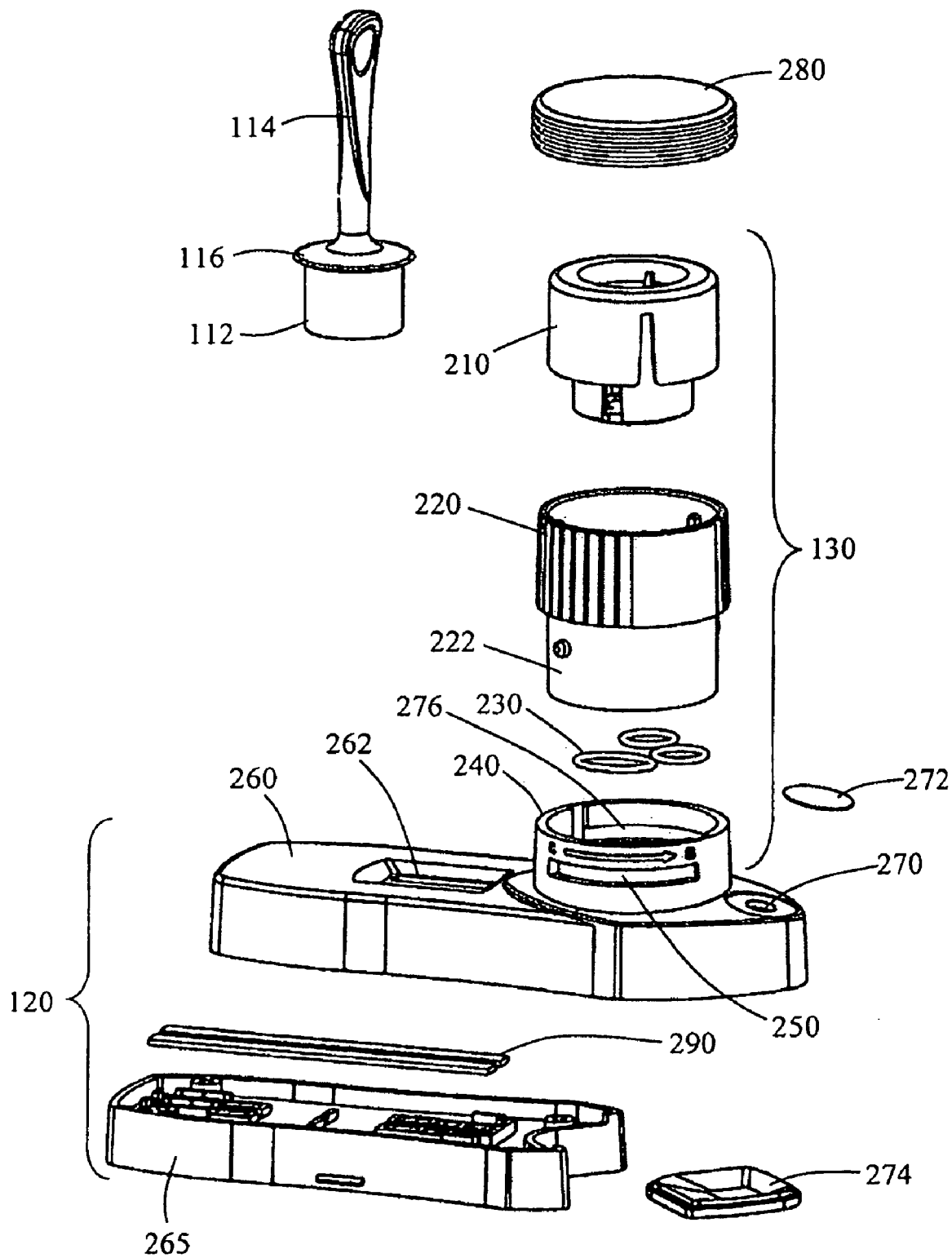
FIG. 2 provides an exploded view of the device of FIG. 1.

With reference to FIGS. 2 and 3, in this embodiment the sample collection well 130 is composed of a sleeve 220, and an annular expresser 210 adapted to fit snugly therein, and a cuff 240. The sample collection well 130 is situated in a port 276 on the upper part 260 of the casing. The cuff 240 is integral to the upper part 260 of the casing, and has a guide slot 250 cut therein in parallel to the upper rim of the cuff. The sleeve 220 has a one guide pin 320 extending from its exterior surface 222 through the guide slot 250 of the cuff. Two or more guide slots 250 and guide pins 320 can be located on the cuff and sleeve. The sleeve and cuff are adapted so that the sleeve fits snugly within cuff and the sleeve can be rotated therein. The rotation of the sleeve within the cuff is guided by the guide slot 250 and the guide pin because the pin cannot move past the bounds of the slot 250.

With reference to FIG. 5, a test compartment inlet 540 and a reservoir inlet 530 are located within the upper part 260 of the casing. The test compartment inlet 540 provides a passageway for fluid to flow into the test compartment from the sample collection well. The test compartment is not air-tight, and air displaced by in-flowing fluid can flow out through cracks between the upper and lower portions. The reservoir inlet 530 provides a passageway for fluid to flow into the reservoir. The reservoir can be air-tight, and can thus have air holes (not shown) for the displaced air to leave the reservoir inlet 530. In one embodiment the air holes are one or more small holes adjacent to the reservoir inlet 530 (for example a small hole on either side of the reservoir inlet). Thus, fluid flows into the reservoir while air escapes through the small holes.

The bottom 336 of the sample collection well has an aliquot outlet 330 and a reservoir outlet 332, for providing passage from the sample collection well to the test compartment and reservoir, respectively. In certain embodiments, the sleeve has first and second positions. The reservoir outlet 332 and aliquot outlet 330 are advantageously located on the bottom of the sample collection well so that when the sleeve is in the first position, the reservoir outlet is open, and therefore the reservoir is in fluid communication with the lower chamber of the sample collection well 130. When the sample collection well is in the first position, fluid expressed from the absorbent member 112 of the sample collector 110 flows through the expression plate 340, through the reservoir outlet 332, and into the reservoir 310. When the sample collection well is in the first position, fluid cannot flow into the test compartment because the aliquot outlet is not in fluid communication with expression plate.

Figure 6:
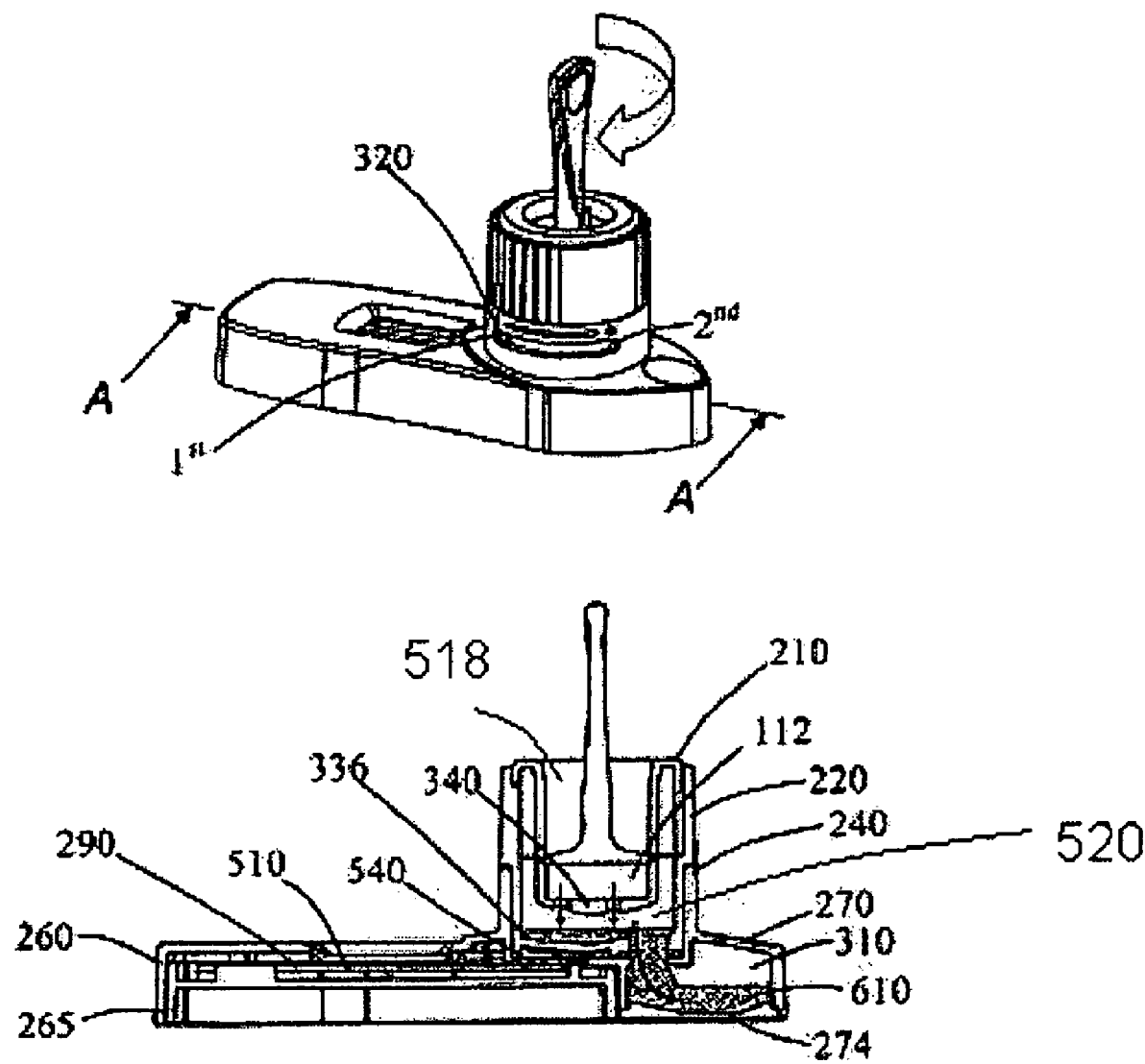
FIG. 6 provides an exterior view and a cut-away view of the device of FIG. 1, illustrating the state of the device during the expression of the sample 610 from the absorbent member 112.
Figure 7:
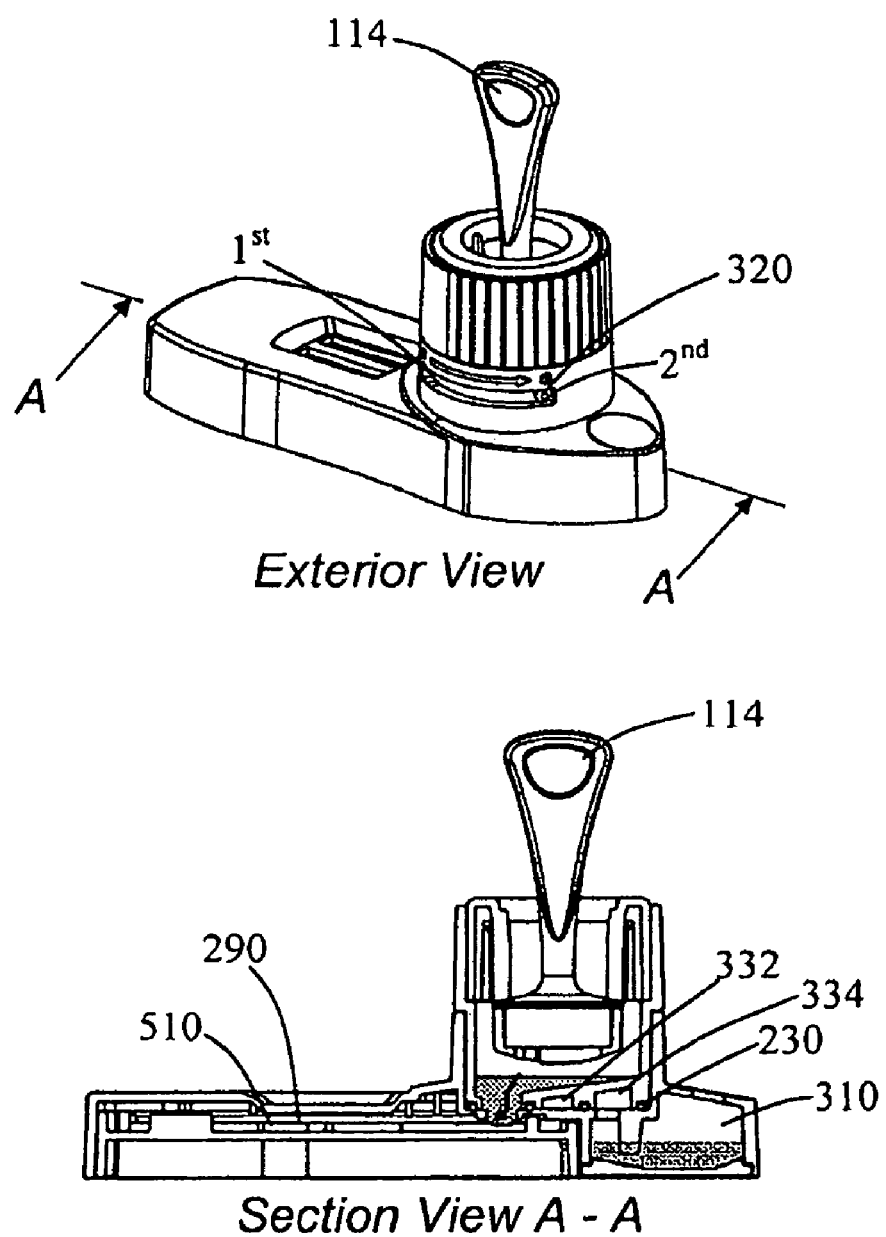
FIG. 7 an exterior view and a cut-away view of the device of FIG. 1, illustrating the state of the device after during release of the sample 610 into the test compartment and sealing of the reservoir 520.

Sample collection well 130 can be rotated to the second position (see FIGS. 5-7). When the sample collection well is in the second position, the aliquot outlet 330 is aligned with the test compartment inlet 540, and the test compartment is placed into fluid communication with the sample collection well. Once the sample collection well is in the second position, fluid expressed from the absorbent member 112 flows through the expression plate, through the aliquot outlet 330 and test compartment inlet 540, into the test compartment and onto the test strips.

The bottom 336 of the sample collection well can also have a reservoir seal 334, which is advantageously sized and placed so that when sample collection well is in the second position the reservoir seal seals the reservoir inlet 530, as well as any air holes adjacent to the reservoir inlet (which may be provided to allow air to escape as fluid sample enters the reservoir). In certain embodiments, an O-ring 230 is mounted on the aliquot outlet, reservoir outlet 322 and reservoir seal 334 (See FIG. 3).

Sample Applicator

A sample applicator may be supplied with the device of the present invention. In one embodiment, the sample applicator has an absorbent member and a handle. The absorbent member is generally made of medical grade sponge or foam material commonly used in the art. But many other materials are available for use as an absorbent member, such as cotton or paper, or any material having suitable absorbent capacity. The handle is generally rigid, to facilitate manipulation of the absorbent member. The handle may be made of any material commonly employed in the art, such as plastic, wood, metal or cardboard. In one embodiment the handle has a rim 116 (FIG. 1) to which the absorbent member is attached.

Test Strips

A variety of test strips can be incorporated into the present invention. Analyte test strips are provided in a variety of formats, such as immunoassay or chemical test format, for detecting analytes of interest in a sample, such as a drug of abuse or a metabolite suggestive of health status. In some formats, the test strips have a bibulous material having a sample application zone, a reagent zone and a test result zone.

The sample is applied to the sample application zone and flows into the reagent zone by capillary action. In the reagent zone, the sample dissolves and mixes with reagents necessary for detection of the analyte (if it is present in the sample). The sample, now carrying the reagents, continues to flow to the test results zone. Additional reagents are immobilized in the test results zone. These reagents react with and bind the analyte (if present) or one of the first reagents from the reagent zone. In noncompetitive formats, a signal is produced if the sample contains the analyte, and no signal is produced if the analyte is not present. In competitive formats, a signal may be produced if no analyte is present, and no signal if analyte is present. The present invention is useful for all formats.

When the test element is a test strip, it may be made of bibulous or non-bibulous material. A test strip can include more than one material, which are then in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. The material or materials of the test strip can be bound to a support or solid surface such as a supporting sheet of plastic, to increase its handling strength.

In embodiments where the analyte is detected by a signal producing system, such as by one or more enzymes that specifically react with the analyte, one or more components of the signal producing system can be bound to the analyte detection zone of the test strip material in the same manner as specific binding members are bound to the test strip material, as described above. Alternatively or in addition, components of the signal producing system that are included in the sample application zone, the reagent zone, or the analyte detection zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the analyte detection zone of the test strip, or that are included throughout the test strip, may be applied to the surface of one or more test strip materials of the test strip as was described for labeled reagents.

The zones can be arranged as follows: sample application zone, one or more reagent zones, one or more test results determination zones, one or more control zones, one or more adulteration zones, and fluid absorbing zone. If the test results determination zone includes a control zone, preferably it follows the analyte detection zone of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication, overlapped to be in fluid communication, or be communicated by another member, such a joining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication.

When and if a test strip includes an adulteration control zone, the adulteration control zone can be placed before or after the results determination zone. When a control zone is present in the results determination zone on such a test strip, then the adulteration control zone is preferably before the control zone, but that need not be the case. In the embodiment of the present invention where a test strip is a control test strip for the determination of an adulteration analyte and/or a control, then the adulteration control zone can be placed before or after the control zone, but is preferably before the control zone.

Samples that can be tested with the device of the present invention include liquids of biological origin (e.g., casing fluids and clinical samples). Liquid samples may be derived from solid or semi-solid samples, including feces, biological tissue, and food samples. Such solid or semi-solid samples can be converted into a liquid sample by any suitable method, for example by mixing, chopping, macerating, incubating, dissolving or enzymatically digesting solid samples in a suitable liquid (e.g., water, phosphate-buffered saline, or other buffers). "Biological samples" include samples derived from living animals, plants, and food, including for example urine, saliva, blood and blood components, cerebrospinal fluid, vaginal swabs, semen, feces, sweat, exudates, tissue, organs, tumors, tissue and organ culture, cell cultures and conditioned media therefrom, whether from humans or animals. A preferred biological sample is urine. Food samples include samples from processed food components or final products, meat, cheese, wine, milk and drinking water. Plant samples include those derived from any plant, plant tissue, plant cell cultures and conditioned media therefrom. "Environmental samples" are those derived from the environment (e.g., a water sample from a lake or other casing of water, effluent samples, soil samples, ground water, ocean water, and runoff water. Sewage and related wastes can also be included as environmental samples.

Any analyte can be tested for utilizing the present invention and a suitable test element. In particular, the present invention can be utilized for the detection of a drug of abuse in saliva.

For example, analytes that can be tested using the present invention include but are not limited to creatinine, bilirubin, nitrite, protein (nonspecific), hormones (e.g. human chorionic gonadotropin, luteinizing hormone, follicle stimulating hormone, etc.), blood, leukocytes, sugar, heavy metals or toxins, bacterial components (e.g. proteins or sugars specific to a particular type of bacteria, such as *E. coli*O157:H7, *S. aureus, Salmonella, C. perfringens, Campylobacter, L. monocytogenes, V. parahaemolyticus,* or *B. cereus*) and physical characteristics of the urine sample, such as pH and specific gravity. Any other clinical urine chemistry analyte that can be adapted to a lateral flow test format may also be incorporated into the present device.

Methods of Use

The invention also provides methods of detecting the presence of an analyte in a fluid sample, using the device described herein. FIGS. 5 through 8 illustrate some of the steps of these methods. FIG. 5 illustrates one embodiment, wherein the absorbent member 112 of the sample applicator has been saturated with sample by placing in the mouth of a test subject. The sample applicator is shown about to be inserted into the sample collection well 130. Note in the exterior view that the sample collection well 130 is in the first position, shown by the location of the guide pin 320 on the side of the guide slot (denoted by 1"). In the section view, it can be seen that when the sample collection well 130 is in the first position, the reservoir outlet 332 and the reservoir inlet 530 are aligned, forming a passage for fluid communication between the lower chamber 520 of the sample collection well 130 and the reservoir 310. Additionally, the test compartment inlet 540 and the test compartment 510 are closed.

FIG. 6 illustrates another embodiment, wherein the sample applicator has been inserted into the sample collection well and against the expression plate 340. The sample applicator is pressed downward against the expression plate 340, thereby wringing or squeezing the absorbent member of the sample applicator, causing fluid 610 contained within the absorbent member to be expressed into the sample collection well. Fluid passing through the expression plate 340 is denoted by downward-pointing arrows. Expressed fluid is denoted by grey shading. Optionally, the expression plate 340 may have two or more vertical ribs 570 under which the rim of the sample applicator may be twisted, to ensure sufficient compression of the absorbent member. The expressed fluid passes through the holes or orifices in the expression plate 340 to the lower chamber 520 of the sample collection well. As discussed, when the sample collection well is in the first position, the reservoir outlet 332 is aligned with the reservoir inlet 530. In this embodiment, the aliquot outlet 330 is closed when the collection well is in the first position. Thus, the fluid in the lower chamber 520 of the sample collection well flows through aligned reservoir outlet 332 and reservoir inlet 530. Air within the reservoir 310 being displaced by incoming fluid escapes into the bottom of the sample collection well through holes in the bottom plane of the sample collection well adjacent to the reservoir inlet 530.

In FIG. 7, the sample collection well has been rotated to the second position. In the exterior view, it can be seen that the guide pin 320 has moved to the end to the guide slot denoted 2nd. When the guide pin 320 is at the 2nd position in the guide slot, the reservoir outlet 332 is closed and the reservoir inlet 530 sealed by the reservoir seal 334 (FIG. 3 ). Additionally, the aliquot outlet 330 and the test compartment inlet 540 are in alignment and mated, so that the test elements 290 are in fluid communication with the lower chamber 520 of the sample collection well. Thus, fluid remaining in the lower chamber 520 of the sample collection well flows into the test compartment 510 and contacts the test strips. When the sample fluid comes into contact with the test strips, the fluid is absorbed by the test strips and the assay begins. Assay times will vary depending on the sample consistency and the test element used.

Figure 8:
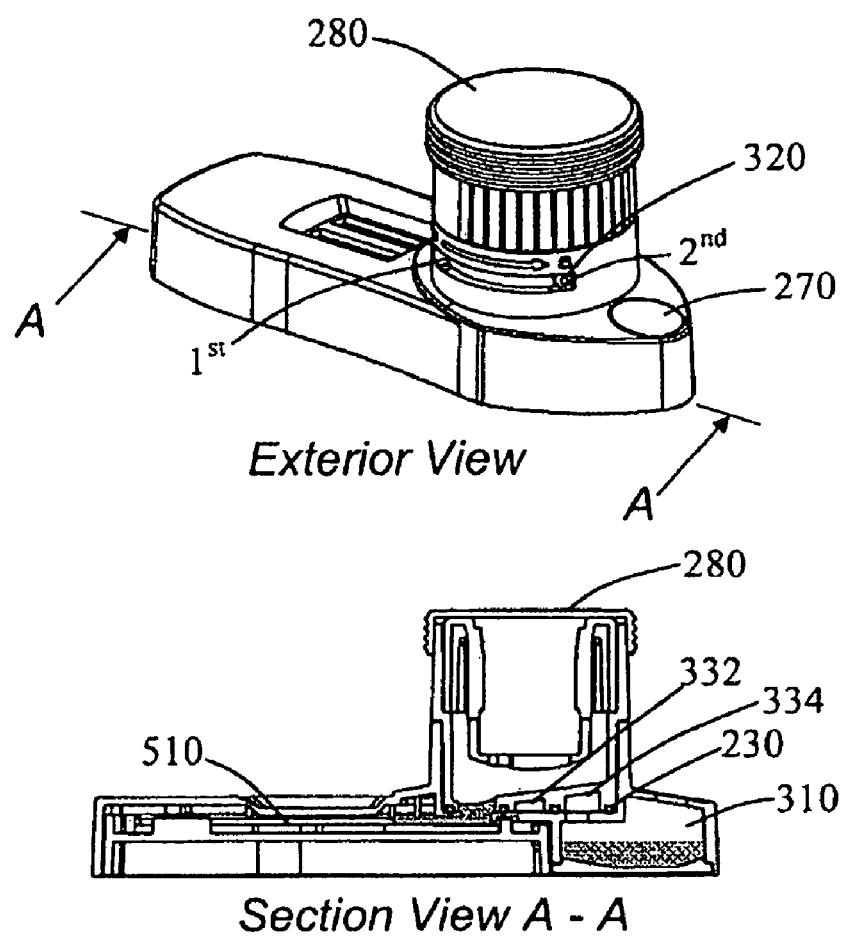
FIG. 8 an exterior view and a cut-away view of the device of FIG. 1, illustrating the state of the device after the device has been capped.

FIG. 8 illustrates another (and optional) step of using the device of the present invention, capping the device. As shown in FIG. 8, the sample collection well is left in the $2^{nd}$ position. Cap 280 is placed on top of the sample collection well. The reservoir is still sealed. The device may now be shipped to another location for confirmation testing. For confirmation testing, the orifice seal 272 can be removed or broken and an aliquot of sample removed from the reservoir via the orifice 270.

The test kits of the invention are provided with a sample applicator. In certain embodiments, instructions for using the device to detect the presence of an analyte in saliva or oral fluid, or other types of fluid, are also provided in the kit. The package format is variable, depending upon the customer's needs. For example, a facility that conducts large numbers of pre-employment drug screenings may prefer boxes of 1 set of instructions plus 20 vacuum packed set of devices and applicators, whereas other facilities may prefer boxed kits that contain only one device, one sample collector and one set of instructions.

EXAMPLES

Example 1

Analytical Sensitivity

This example illustrates the analytical sensitivity of the devices and methods of the invention. Ten devices were tested with each sample solution, for a total of 300 tests. The devices were tested with normal saliva, and using test strips that had the antigen affixed thereto for the drugs of abuse being tested for. The test strips functioned in a competitive format, with multiple gold sol-labeled antibodies present in a label zone, and antigens present on the test line.

The devices were also tested with PBS spiked with a standard solution of Cocaine (COC), Methamphetamine (MAMP), Phencyclidine (PCP), tetrahydrocannabinol (THC), morphine (MOP) or amphetamine (AMP) at concentrations of 0×, 0.5×, 1.5× and 3× times the detection limit. For example, the detection limit of the saliva THC test is 4 ng/ml. So PBS containing 0 ng/ml, 2 ng/ml, 6 ng/ml and 8 ng/ml of THC were tested. For convenience, the amounts of drugs tested are shown in the table below.

| Drug (Detection Limit) | Saliva | PBS | PBS + 0.5X Drug | PBS + 1.5X Drug | PBS + 3X Drug |
| --- | --- | --- | --- | --- | --- |
| COC (20 ng/ml) | 0 ng/ml | 0 ng/ml | 10 ng/ml | 30 ng/ml | 60 ng/ml |
| MAMP (50 ng/ml) | 0 ng/ml | 0 ng/ml | 25 ng/ml | 75 ng/ml | 150 ng/ml |
| PCP (10 ng/ml) | 0 ng/ml | 0 ng/ml | 5 ng/ml | 15 ng/ml | 30 ng/ml |
| THC (4 ng/ml) | 0 ng/ml | 0 ng/ml | 2 ng/ml | 6 ng/ml | 12 ng/ml |
| MOP (40 ng/ml) | 0 ng/ml | 0 ng/ml | 20 ng/ml | 60 ng/ml | 120 ng/ml |
| AMP (50 ng/ml) | 0 ng/ml | 0 ng/ml | 25 ng/ml | 75 ng/ml | 150 ng/ml |

To perform each test, saliva, PBS or spiked PBS, as described above, was absorbed into the absorbent sponge of the sample applicator and then expressed into the sample collection well of the test device. Next, the sample well was rotated from the first position to the second position. After the sample well was rotated to the second position, the test strips were observed to become wet and the fluid to wick through the test strips. The test results were recorded at ten minutes and are shown in the table below.

| Drug | Saliva | PBS | PBS + 0.5X Drug | PBS + 1.5X Drug | PBS + 3X Drug | % Correct Result |
| --- | --- | --- | --- | --- | --- | --- |
| COC | negative | negative | weak neg. | positive | very strong pos. | 100% |
| MAMP | negative | negative | weak neg. | positive | very strong pos | 100% |

-continued

| Drug | Saliva | PBS | PBS + 0.5X Drug | PBS + 1.5X Drug | PBS + 3X Drug | % Correct Result |
|------|--------|-----|-----------------|-----------------|---------------|------------------|
| PCP | negative | negative | weak neg. | positive | very strong pos | 96% |
| THC | negative | negative | weak neg. | positive | very strong pos | 100% |
| MOP | negative | negative | weak neg. | positive | very strong pos | 100% |
| AMP | negative | negative | weak neg. | positive | very strong pos | 100% |

Test results demonstrated that the device of the present invention is very sensitive and provided the expected cutoff ranges.

Example 2

Sample Size Variability

This example illustrates the effect of sample size on the performance of the present device. Replicates of five devices were tested with the same drugs tested in Example 1, at 0×, 0.5× and 3× concentrations (made in PBS as described above). Sample volumes of 100 ul, 150 ul, 200 ul and 250 ul were pipetted into the devices, instead of applying the sample with the sample applicator. All results were read as positive (pos) or negative (neg) at 10 minutes after sample application. With the exception of the 0.5 ×THC test at 250 ul (which provided 4 out of 5 identical results), all five replicates in each test group gave identical results. Therefore, the devices are able to provide a correct result even with considerable variability in sample volume.

Example 3

Pre-Employment Drug Screening

The devices of the invention can be utilized in a variety of contexts, for example, for pre-employment drug screening. The person to be tested provides a sample of saliva by placing the sample applicator into his or her mouth, and allowing it to remain in the mouth for about 5 minutes. In embodiments for pre-employment drug screening the device contains test strips for several common drugs of abuse, in this embodiment cocaine, methamphetamine, phencyclidine, THC, morphine, and amphetamines. These test strips utilize a competitive immunoassay format where labeled specific binding molecules (antibodies in this embodiment) for each drug being tested are present on the label zone of the test strip. The test lines contain the antigen being tested for. If analyte is present in the sample it is bound by labeled specific binding molecules in the label zone, thereby preventing the labeled antibody from binding to the test line. Thus, no signal occurs on the test line when analyte is present. Conversely, when no antigen is present in the saliva, the labeled antibodies bind to the test line providing the signal on the test line.

After receiving the filled or soaked sample applicator, the testing technician inserts it into the sample collection well of the device. The technician presses the applicator down into the well and then twists it, to lock the rim of the applicator under a pair a flanges (provided in this embodiment). Saliva is thereby expressed from the absorbent foam of the sample applicator and flows through holes in the expression plate and into the lower chamber of the sample collection well. Since the collection well is in the first position, sample also flows through the reservoir outlet and into the reservoir. When all of sample is loaded and the reservoir contains sufficient sample to conduct a confirmation assay, the sample collection well is then turned from the first position to the second position, thereby sealing the reservoir and opening the aliquot outlet. Sample then flows into the test strips. After a few minutes, the control indicia are provided, indicating that the assay is complete. A signal is provided at each of the test lines, indicating that no drugs of abuse are present in the saliva sample. If a positive result is determined, the device may be sent to a confirmatory laboratory so that the sample contained in the reservoir can be tested to confirm the result.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

We claim:

1. A test device for detecting an analyte suspected of being present in a liquid sample, comprising:
   a casing comprising a sealable reservoir compartment, a test compartment, and a port, wherein at least one test element is comprised within the test compartment;
   a rotatable sample collection well, situated in the port and comprising an upper chamber, an expression plate, a lower chamber, an aliquot outlet, and a reservoir outlet; and
   wherein
   the rotatable sample collection well has a first position where fluid communication is provided through the reservoir outlet between the rotatable sample collection well and the reservoir compartment of the casing and wherein the aliquot outlet is closed; and
   the rotatable sample collection well has a second position where fluid communication is provided through the aliquot outlet between the rotatable sample collection well and the test compartment and wherein the reservoir outlet is closed.

2. The device of claim 1, wherein the lower chamber comprises an area between the bottom of the rotatable sample collection well and the expression plate.

3. The device of claim 2 wherein the aliquot outlet and the reservoir outlet are situated on the bottom of the rotatable sample collection well.

4. The device of claim 3 wherein the rotatable sample collection well further comprises an aliquot seal, for sealing of the aliquot reservoir when the rotatable sample collection well is located in the first position.

5. The test device of claim 4 wherein the port comprises a guide slot, and the rotatable sample collection well comprises a guide pin extending from its outer surface and movably located within the guide slot, for directing rotation of the rotatable sample collection well from the first position to the second position.

6. The device of claim 5 wherein the guide slot is substantially parallel to the longitudinal axis of the test element.

7. The test device of claim 1 wherein the expression plate comprises openings through which fluid sample can flow from the upper chamber to the lower chamber.

8. The test device of claim, 1 the casing further comprising a window for observation of the test element.

9. The test device of claim, 1 wherein the casing further comprises a sealable reservoir orifice for extracting liquid sample from the reservoir compartment.

10. The test device of claim, 1 wherein the test element is a test strip.

11. The device of claim 10 wherein the test strip comprises specific binding molecules immobilized on the test strip.

12. The device of claim 10 wherein the test strip further comprises a chemical test.

13. The test device of claim 1 wherein the sample is a bodily fluid or derived from a tissue or a bodily fluid.

14. The test device of claim 1 wherein the sample is selected from the group consisting of saliva, blood, serum, plasma, urine, feces, spinal fluid, vaginal swabs, mucus, and tissue.

15. The test device of claim 14 wherein the sample further comprises saliva.

16. The test device of claim 1 wherein the analyte is an infectious agent or indicative of an infected state.

17. The test device of claim 1 wherein the analyte of interest is selected from the group consisting of a drug, a drug of abuse, a hormone, a protein, a nucleic acid molecule, an etiological agent and a specific binding member.

18. The test device of claim 1, wherein the analyte is a drug of abuse.

19. The test device of claim 1 wherein the rotatable sample collection well is comprised of two or more parts, a first part containing the upper chamber and the expression plate, and a second part containing the lower chamber.

* * * * *